United States Patent
Webster et al.

(10) Patent No.: US 7,462,198 B2
(45) Date of Patent: Dec. 9, 2008

(54) MOBILE BEARING UNICONDYLAR TIBIAL KNEE PROSTHESIS

(75) Inventors: Vincent A. Webster, Warsaw, IN (US); Scott J. Steffensmeier, Warsaw, IN (US); Adam H. Sanford, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 165 days.

(21) Appl. No.: 11/262,448

(22) Filed: Oct. 28, 2005

(65) Prior Publication Data

US 2006/0036329 A1    Feb. 16, 2006

Related U.S. Application Data

(60) Division of application No. 10/818,107, filed on Apr. 5, 2004, now Pat. No. 7,033,397, which is a continuation-in-part of application No. 10/357,264, filed on Feb. 3, 2003, now Pat. No. 6,946,001.

(51) Int. Cl.
*A61F 2/38* (2006.01)
(52) U.S. Cl. .................................. 623/20.3; 623/20.29
(58) Field of Classification Search .............. 623/20.29, 623/20.3, 20.33
See application file for complete search history.

(56) References Cited

U.S. PATENT DOCUMENTS

| 5,282,868 | A | * | 2/1994 | Bahler | ..................... 623/20.29 |
| 5,336,266 | A | | 8/1994 | Caspari | |
| 5,871,541 | A | * | 2/1999 | Gerber | ..................... 623/20.29 |
| 5,871,542 | A | | 2/1999 | Goodfellow | |
| 6,102,954 | A | | 8/2000 | Albrektsson | |

FOREIGN PATENT DOCUMENTS

| EP | 1097679 A | 5/2001 |
| EP | 1136045 A | 9/2001 |
| WO | WO 93/22990 | 11/1993 |

* cited by examiner

*Primary Examiner*—Bruce E. Snow
(74) *Attorney, Agent, or Firm*—Baker & Daniels LLP

(57) ABSTRACT

A mobile bearing unicondylar tibial knee prosthesis includes a tibial base plate and a tibial articular surface component. The inferior surface of the articular surface component engages the superior surface of the base plate in sliding relationship. The tibial articular surface and a stop on the tibial base plate define a tab and groove engagement between them such that the tibial articular surface component is permitted to slide anteriorly-posteriorly on the tibial base plate while movement of the tibial articular surface component superiorly away from the base plate is restricted.

9 Claims, 6 Drawing Sheets

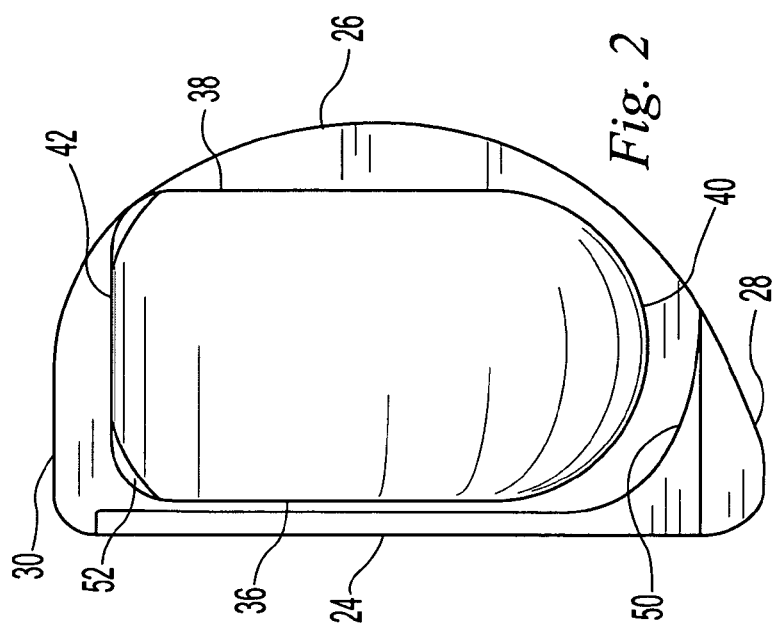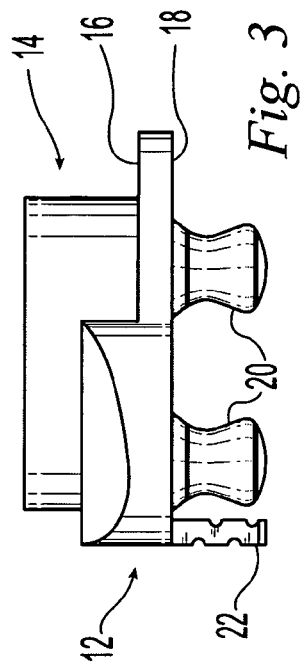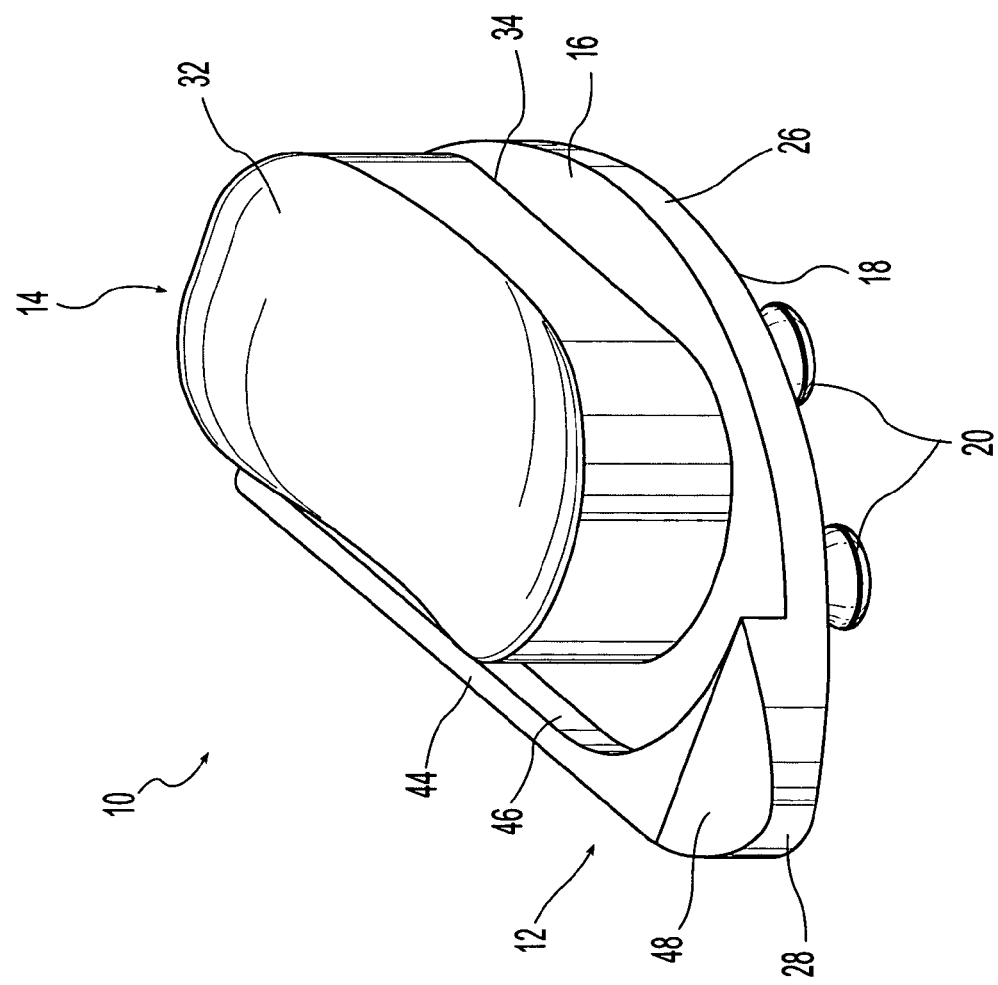

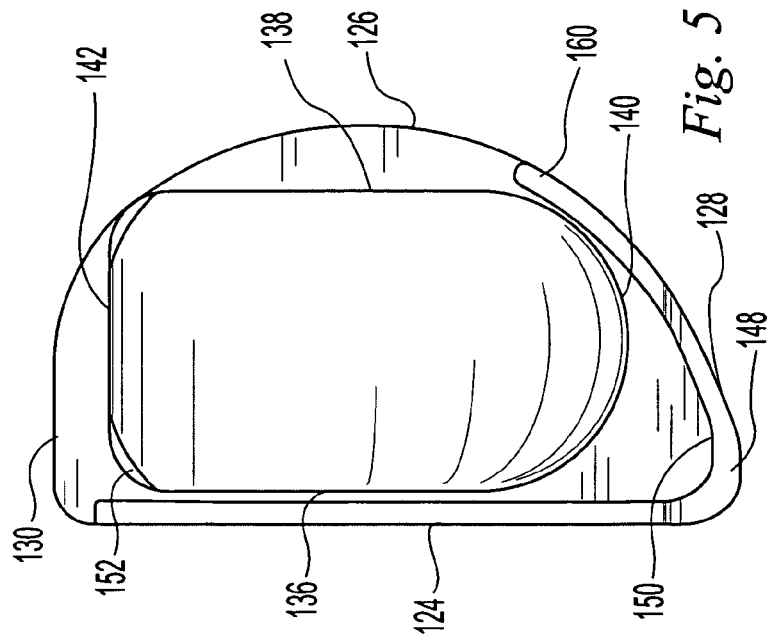
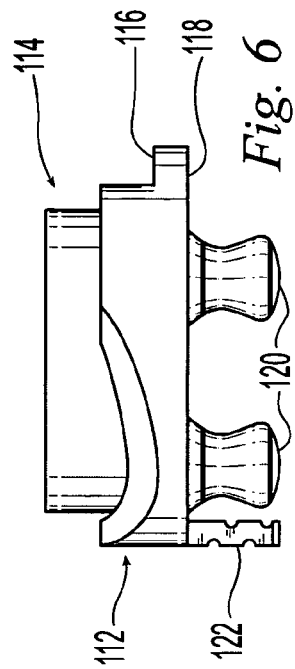
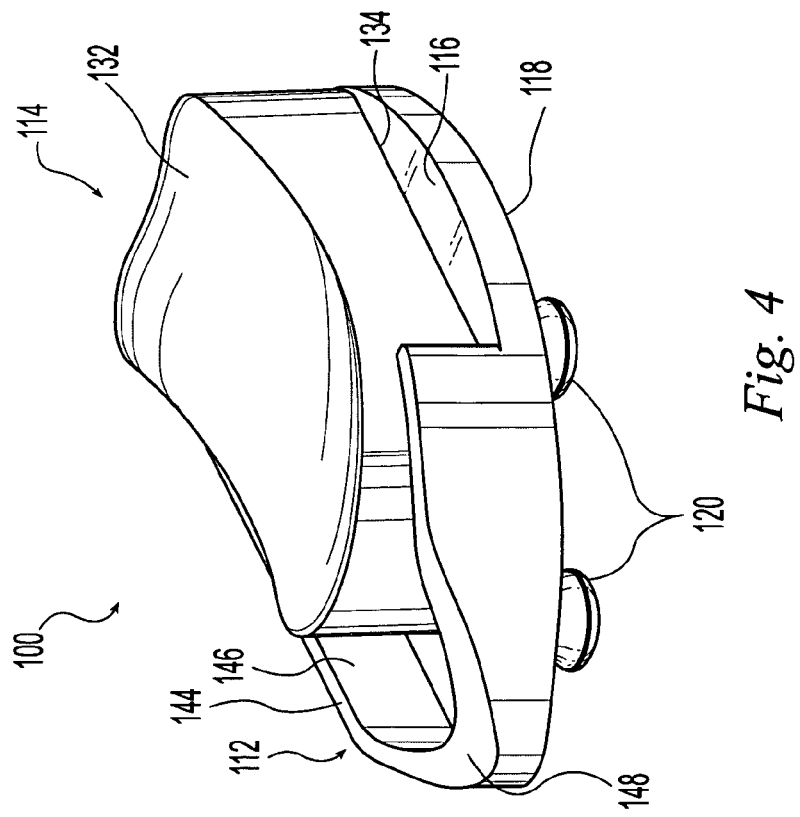

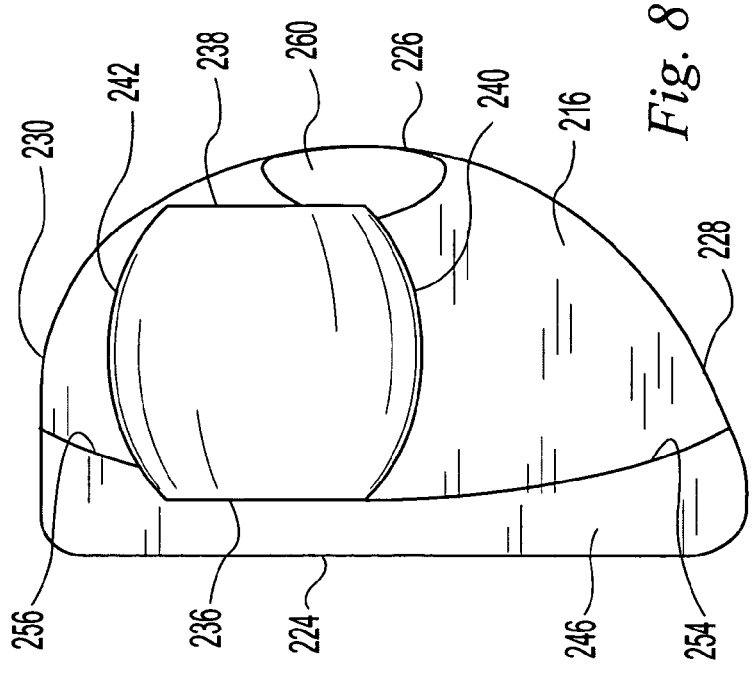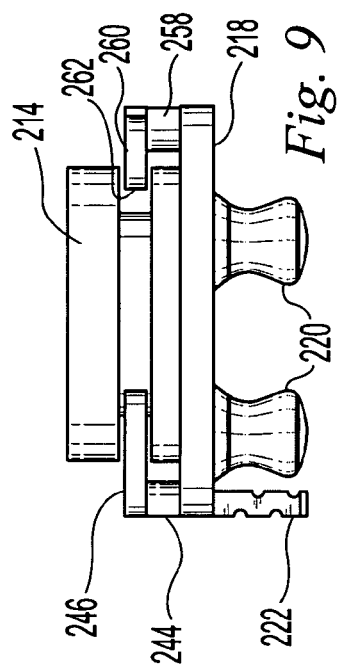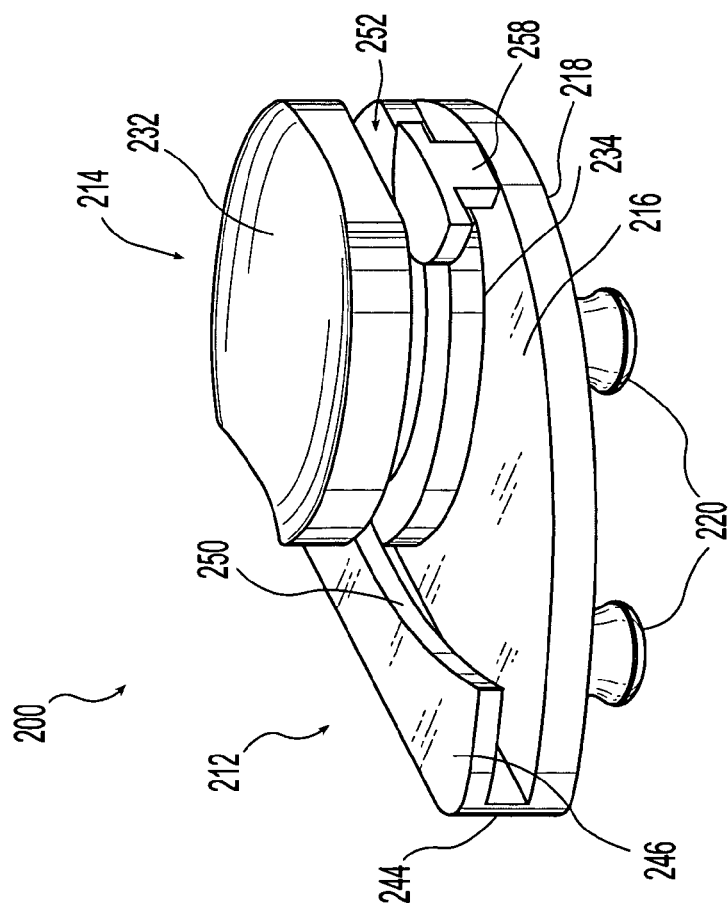

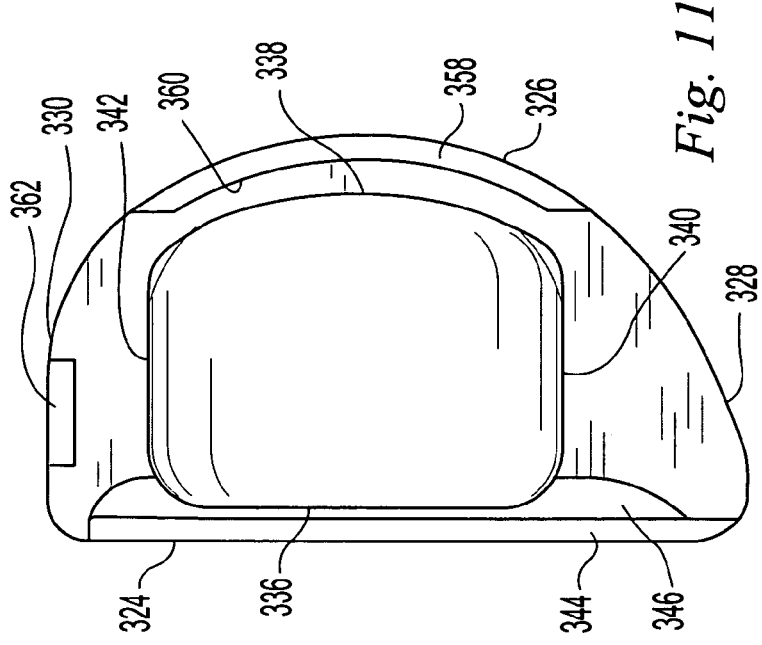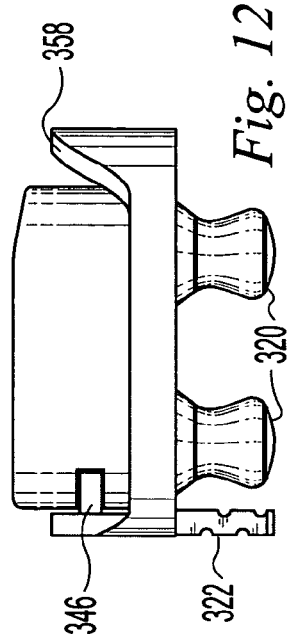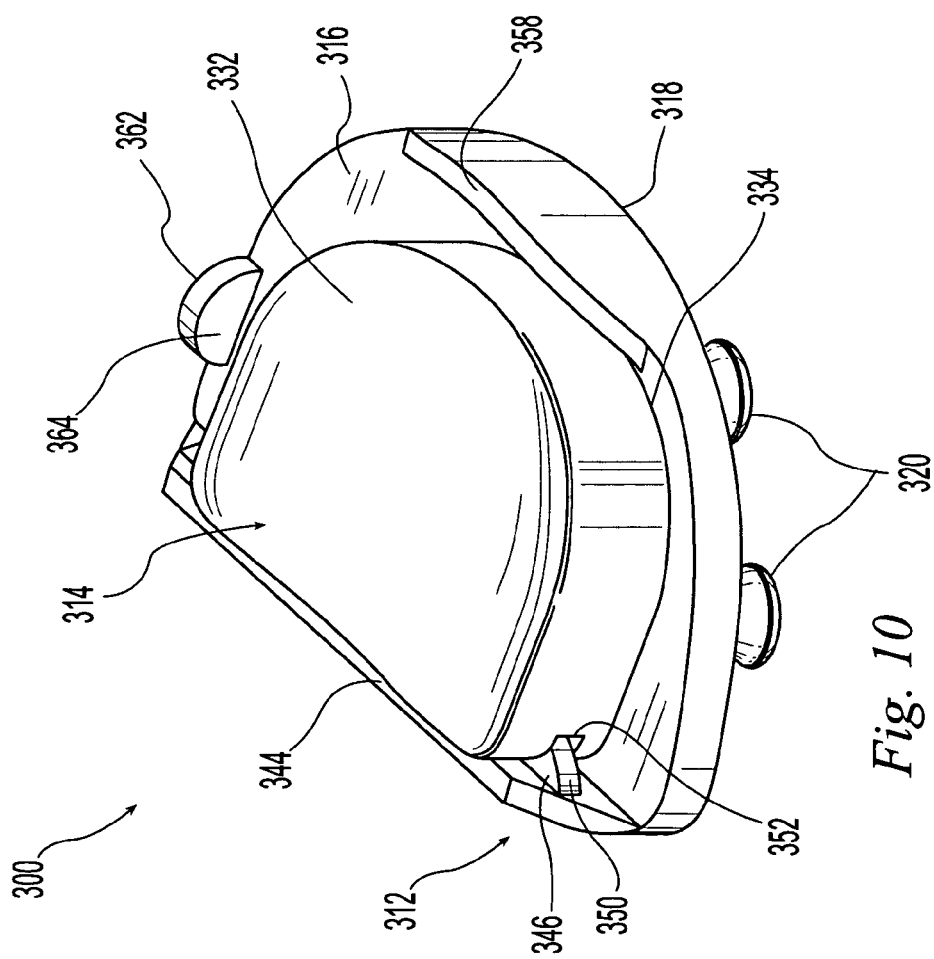

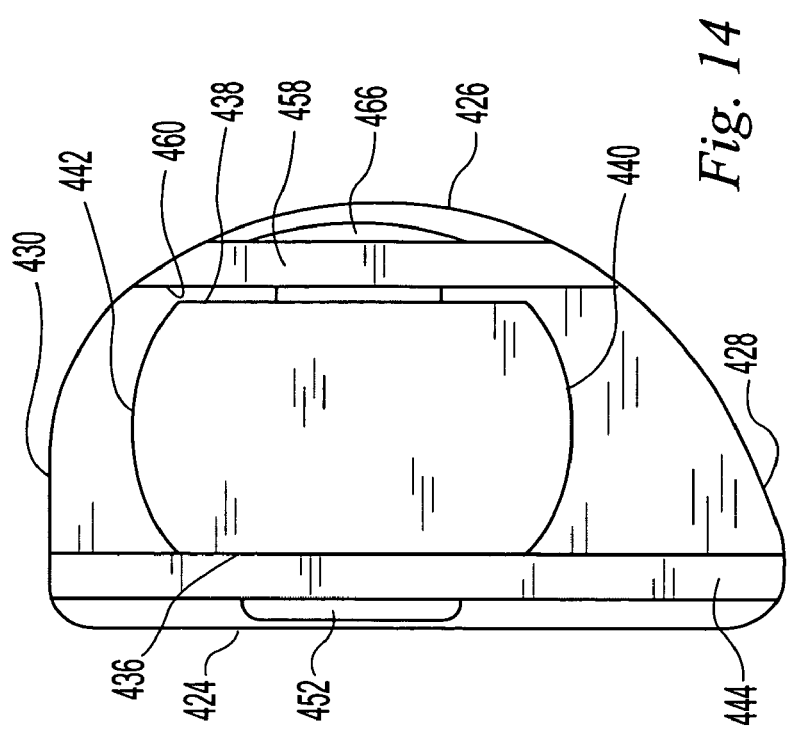

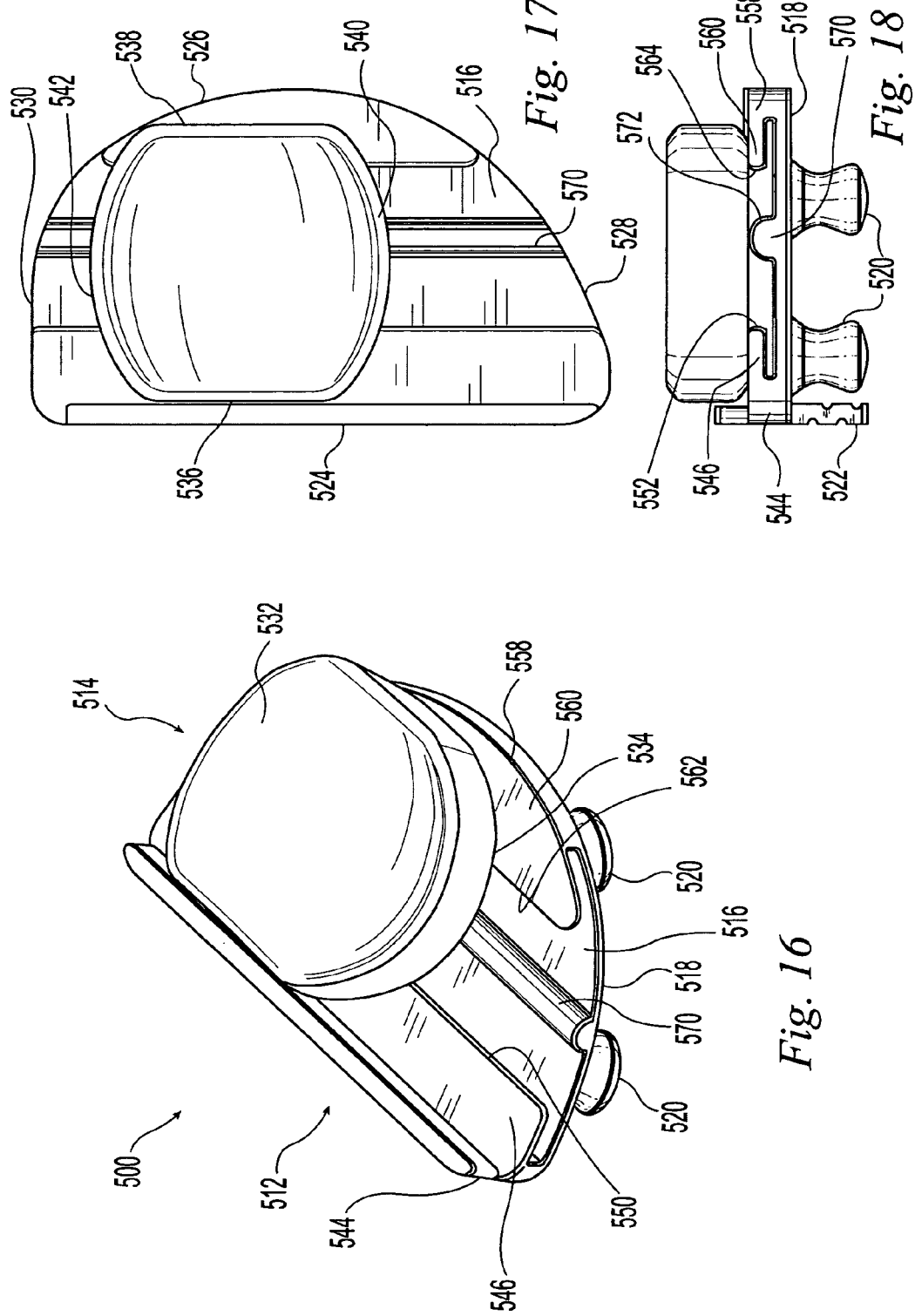

MOBILE BEARING UNICONDYLAR TIBIAL KNEE PROSTHESIS

CROSS-REFERENCE TO RELATED APPLICATIONS

This application is a division of U.S. application Ser. No. 10/818,107 filed on Apr. 5, 2004, now U.S. Pat. No. 7,033,397, which is a continuation-in-part of U.S. application Ser. No. 10/357,264, filed Feb. 3, 2003 now U.S. Pat. No. 6,946,001.

FIELD OF THE INVENTION

The invention relates to mobile bearing knee prostheses. More particularly the invention relates to mobile bearing unicondylar tibial knee prostheses.

BACKGROUND

Degenerative and traumatic damage to the articular cartilage of the knee joint can result in pain and restricted motion. Prosthetic joint replacement is frequently utilized to alleviate the pain and restore joint function. In a total knee replacement, all of the articulating compartments of the joint are repaired with prosthetic components. However, often only one compartment of the knee joint, typically the medial compartment, is impaired. Thus, in a unicondylar knee replacement, only the damaged compartment is repaired with prosthetic bearing components. Unicondylar knee replacement can be less invasive and can have a shorter recovery time than total knee replacement. In repairing the damaged portions of the knee, it is desirable to restore the joint as nearly as possible to normal anatomic functioning.

SUMMARY

The present invention provides a mobile bearing unicondylar tibial knee prosthesis for repairing a damaged knee joint.

The mobile bearing unicondylar tibial knee prosthesis includes a tibial base plate and a tibial articular surface component. The inferior surface of the articular surface component engages the superior surface of the base plate in sliding relationship. The tibial articular surface and a stop on the tibial base plate define a tab and groove engagement between them such that the tibial articular surface component is permitted to slide anteriorly-posteriorly on the tibial base plate while movement of the tibial articular surface component superiorly away from the base plate is restricted.

In another aspect of the invention, the tibial base plate further includes a rail that curves toward the outside edge at an anterior portion and at a posterior portion. The curved anterior and posterior portions cause the articular surface component to slide outwardly away from the inside edge of the base plate at anterior and posterior positions of the articular surface component on the base plate such that the articular surface component is constrained generally to arc-shaped motion.

In another aspect of the invention, the base plate further includes a rib projecting superiorly from the superior surface of the base plate between the inside and outside edges of the plate. The rib extends from near the anterior aspect to near the posterior aspect of the plate and the articular surface component includes a corresponding groove engageable with the rib formed in the inferior surface of the articular surface component.

In another aspect of the invention, the base plate further includes an outer stop having a concave, inwardly directed face. The articular surface component abuts the outer stop to limit the articular surface components outward movement to motion within a "D"-shaped area.

These and other aspects of the invention will be described with reference to the drawings.

BRIEF DESCRIPTION OF THE DRAWINGS

Various embodiments of the present invention are described with reference to the appended drawings. These drawings depict only illustrative embodiments of the invention and are not to be considered limiting of its scope.

FIG. 1 is a perspective view of an illustrative mobile unicondylar tibial knee prosthesis according to the invention;

FIG. 2 is a top plan view of the prosthesis of FIG. 1;

FIG. 3 is a front plan view of the prosthesis of FIG. 1;

FIG. 4 is a perspective view of an optional configuration of the prosthesis of FIG. 1;

FIG. 5 is a top plan view of the prosthesis of FIG. 4;

FIG. 6 is a front plan view of the prosthesis of FIG. 4;

FIG. 7 is a perspective view of an optional configuration of the prosthesis of FIG. 1 in which the tibial base plate and articular surface component are engaged in tab and groove relationship;

FIG. 8 is a top plan view of the prosthesis of FIG. 7;

FIG. 9 is a front plan view of the prosthesis of FIG. 7;

FIG. 10 is a perspective view of the prosthesis of FIG. 7 showing an alternative arrangement of the tab and groove relationship;

FIG. 11 is a top plan view of the prosthesis of FIG. 10;

FIG. 12 is a front plan view of the prosthesis of FIG. 10;

FIG. 13 is a perspective view of the prosthesis of FIG. 7 showing an alternative arrangement of the tab and groove relationship;

FIG. 14 is a top plan view of the prosthesis of FIG. 13;

FIG. 15 is a front plan view of the prosthesis of FIG. 13;

FIG. 16 is a perspective view of the prosthesis of FIG. 7 showing an alternative arrangement of the tab and groove relationship;

FIG. 17 is a top plan view of the prosthesis of FIG. 16; and

FIG. 18 is a front plan view of the prosthesis of FIG. 16.

DESCRIPTION OF THE ILLUSTRATED EMBODIMENTS

The Mobile Bearing Unicondylar Tibial Knee Prosthesis of the present invention will be explained with reference to FIGS. 1-16. The drawings depict a mobile bearing unicondylar tibial knee prosthesis for replacing one side of the proximal surface of a tibia. The prosthesis depicted in the various drawings is configured for replacing the medial side of a right knee. Similar prostheses may be provided, and are within the scope of the invention, for replacing the lateral side of the right knee as well as the medial and lateral sides of the left knee. In addition, two such prostheses may be used together to replace both sides of the tibia in a multi-component total knee arthroplasty.

FIGS. 1-3 depict an illustrative mobile bearing unicondylar tibial knee prosthesis 10 including a tibial base plate component 12 and a tibial articular surface component 14. The base plate 12 is generally in the form of a generally flat, "D"-shaped plate having a smooth superior surface 16 for sliding engagement with the articular surface component 14 and an inferior surface 18 for engaging the bone. The inferior surface 18 includes pegs 20 and a fin 22 for insertion into the bone for enhanced fixation. The base plate 12 further includes an inside edge 24 that is positioned near the midline of the proximal tibia adjacent to the intercondylar eminence, an outside edge 26 that is positioned adjacent to the outer side (corresponding to the medial side of the knee for the illustrative prosthesis configured for the medial compartment of the knee) of the proximal tibia, an anterior aspect 28 that is positioned adjacent to the anterior side of the proximal tibia, and a posterior aspect 30 that is positioned adjacent to the posterior side of the proximal tibia.

The articular surface component 14 includes a superior surface 32 for articulation with a femoral component (not shown), an inferior surface 34 for sliding engagement with the superior surface 16 of the base plate 12, an inside edge 36, an outside edge 38, an anterior aspect 40, and a posterior aspect 42. The articular surface component 14 rests on the superior surface 16 of the base plate 12 and is generally free to slide from the anterior aspect 28 to the posterior aspect 30 of the base plate 12, to slide from the inside edge 24 to the outside edge 26 of the base plate 12, and to rotate on the base plate 12.

The base plate 12 further includes an inside rail 44 projecting superiorly from the superior surface 16 of the plate 12 to prevent the articular surface component 14 from impinging against the intercondylar eminence of the proximal tibia. The rail 44 presents a generally vertical face 46 extending from near the anterior aspect 28 of the plate 12 to near the posterior aspect 30 of the plate. At the extreme limits of motion of the articular surface component 14 toward the inside edge 24 of the plate 12, the articular surface component 14 will abut some portion of the rail 44, such as the face 46, and stop its inward movement. The base plate 12 further includes an anterior stop 48 projecting superiorly from the superior surface 16 of the plate 12 to prevent the articular surface component 14 from overhanging the anterior aspect 28 of the plate 12. The anterior stop 48 presents a vertical face 50 extending around a portion of the anterior aspect 28 of the plate 12 and connecting to the vertical face 46 of the rail 44. At the extreme limits of anterior motion of the articular surface component 14, the anterior surface component 14 will abut the face 50 of the anterior stop 48 and stop its anterior movement. In the illustrative embodiment, the vertical face 50 of the anterior stop 48 and the anterior aspect 40 of the articular surface component 14 are curved. In the illustrative embodiment, the anterior stop 48 has a concave curve and the anterior aspect 40 of the articular surface component 14 is convex. It is contemplated that the concavity of the curves may be reversed and still be within the scope of the invention. The curves facilitate rotation of the articular surface component 14 on the base plate 12 even when the articular surface component 14 is pressed forward against the anterior stop 48. For example, when the articular surface component 14 has slid against the inside rail 44 and the anterior stop 48, it is still free to pivot about the complimentary curves to permit the posterior aspect 42 of the articular bearing component 14 to move away from the inside rail 44. Alternatively, only one of the anterior stop 48 and anterior aspect 40 of the articular surface component 14 may include a curved surface to facilitate this rotation. Likewise, the junction 52 between the inside edge 36 and posterior aspect 42 of the articular surface component 14 includes a convex curve to facilitate rotation of the anterior aspect 40 of the articular surface component 14 away from the inside rail 44. Finally, the articular surface component 14 may be symmetrical both anterioposteriorly and mediolaterally such that it may be installed with either of the anterior or posterior aspects 40 or 42 forward.

FIGS. 4-6 depict a mobile bearing unicondylar tibial knee prosthesis 100 similar to that of FIGS. 1-3 including a tibial base plate component 112 and a tibial articular surface component 114. The base plate 112 is generally in the form of a generally flat, "D"-shaped plate having a smooth superior surface 116 for sliding engagement with the articular surface component 114 and an inferior surface 118 for engaging the bone. The inferior surface 118 includes pegs 120 and a fin 122 for insertion into the bone for enhanced fixation. The base plate 112 further includes an inside edge 124 that is positioned near the midline of the proximal tibia adjacent to the intercondylar eminence, an outside edge 126 that is positioned adjacent to the outer side (corresponding to the medial side of the knee for the illustrative prosthesis configured for the medial compartment of the knee) of the proximal tibia, an anterior aspect 128 that is positioned adjacent to the anterior side of the proximal tibia, and a posterior aspect 130 that is positioned adjacent to the posterior side of the proximal tibia.

The articular surface component 114 includes a superior surface 132 for articulation with a femoral component, an inferior surface 134 for sliding engagement with the superior surface 116 of the base plate 112, an inside edge 136, an outside edge 138, an anterior aspect 140, and a posterior aspect 142. The articular surface component 114 rests on the superior surface 116 of the base plate 112 and is generally free to slide from the anterior aspect 128 to the posterior aspect 130 of the base plate 112, to slide from the inside edge 124 to the outside edge 126 of the base plate 112, and to rotate on the base plate 112.

The base plate 112 further includes an inside rail 144 projecting superiorly from the superior surface 116 of the plate 112 to prevent the articular surface component 114 from impinging against the intercondylar eminence of the proximal tibia. The rail 144 presents a generally vertical face 146 extending from near the anterior aspect 128 of the plate 112 to near the posterior aspect 130 of the plate. At the extreme limits of motion of the articular surface component 114 toward the inside edge 124 of the plate 112, the articular surface component 114 will abut some portion of the rail 144, such as the face 146, and stop its inward movement. The base plate 112 further includes an anterior stop 148 projecting superiorly from the superior surface 116 of the plate 112 to prevent the articular surface component 114 from overhanging the anterior aspect 128 of the plate 112. The anterior stop 148 presents a vertical face 150 extending around a portion of the anterior aspect 128 of the plate 112 and connecting to the vertical face 146 of the rail 144. At the extreme limits of anterior motion of the articular surface component 114, the anterior surface component 114 will abut the face 150 of the anterior stop 148 and stop its anterior movement. In the illustrative embodiment of FIGS. 4-6, a portion 160 of the anterior stop 148 extends around the anterior aspect 128 of the plate 112 and back toward the posterior aspect 130 of the plate 112 such that the rail and anterior stop 148 form of a generally "J"-shaped constraint wall. In the illustrative embodiment, the anterior stop 148 and the anterior aspect 140 of the articular surface component 114 are curved. These curves facilitate rotation of the articular surface component 114 on the base plate 112 even when the articular surface component 114 is pressed forward against the anterior stop 148. For example, when the articular surface component 114 has slid against the inside rail 144 and the anterior stop 148, it is still free to pivot about the complimentary curves to permit the posterior aspect 142 of the articular bearing component 114 to move away from the inside rail 144.

Likewise, the junction 152 between the inside edge 136 and posterior aspect 142 of the articular surface component 114 includes a convex curve to facilitate rotation of the anterior aspect 140 of the articular surface component 114 away from the inside rail 144. However, rotation of the anterior aspect 140 of the articular surface component 114 away from the inside rail 144 is only possible when the articular surface component 114 is not all the way forward against the anterior stop 148. When the articular surface component 114 is against the anterior stop 148, the portion 160 of the anterior stop 128 extending posteriorly constrains the anterior aspect 140 of the articular surface component 114 to rotation only and does not permit it to translate toward the outside edge 126 of the base plate 112.

FIGS. 7-9 depict a mobile bearing unicondylar tibial knee prosthesis 200 similar to that of FIGS. 1-3 including a tibial base plate component 212 and a tibial articular surface component 214. The base plate 212 is generally in the form of a generally flat, "D"-shaped plate having a smooth superior surface 216 for sliding engagement with the articular surface component 214 and an inferior surface 218 for engaging the bone. The inferior surface 218 includes pegs 220 and a fin 222 for insertion into the bone for enhanced fixation. The base plate 212 further includes an inside edge 224 that is positioned near the midline of the proximal tibia adjacent to the intercondylar eminence, an outside edge 226 that is positioned adjacent to the outer side (corresponding to the medial side of the knee for the illustrative prosthesis configured for the medial compartment of the knee) of the proximal tibia, an anterior aspect 228 that is positioned adjacent to the anterior side of the proximal tibia, and a posterior aspect 230 that is positioned adjacent to the posterior side of the proximal tibia.

The articular surface component 214 includes a superior surface 232 for articulation with a femoral component, an inferior surface 234 for sliding engagement with the superior surface 216 of the base plate 212, an inside edge 236, an outside edge 238, an anterior aspect 240, and a posterior aspect 242. The articular surface component 214 rests on the superior surface 216 of the base plate 212 and is generally free to slide from the anterior aspect 228 to the posterior aspect 230 of the base plate 212, to slide from the inside edge 224 to the outside edge 226 of the base plate 212, and to rotate on the base plate 212.

The base plate 212 further includes an inside rail 244 projecting superiorly from the superior surface 216 of the plate 212 to prevent the articular surface component 214 from impinging against the intercondylar eminence of the proximal tibia. The rail 244 includes an outwardly projecting tab 246 spaced above and parallel to the superior surface 216 of the plate 212. The tab 246 includes a face 250 extending from near the anterior aspect 228 of the plate 212 to near the posterior aspect 230 of the plate and directed toward the articular surface component 214. At the extreme limits of motion of the articular surface component 214 toward the inside edge 224 of the plate 212, the articular surface component 214 will abut some portion of the rail 244, such as the face 250, and stop its inward movement. The articular surface component 214 includes a circumferential groove 252 that receives the tab 246 to prevent the inside edge 236 of the articular surface component 214 from moving vertically away from the base plate 212 such as by tipping. The face 250 of the tab 246 curves toward the outside edge 226 at an anterior portion 254 and a posterior portion 256. These curved portions 254, 256 cause the articular surface component 214 to slide outwardly away from the tibial eminence at extreme anterior and posterior positions of the articular surface component 214 on the base plate 212.

The base plate 212 further includes one or more stops. In the illustrative example, a single outer stop 258 is depicted. However, it is contemplated that a plurality of stops may be included to yield a desired amount of constraint. The outer stop 258 projects superiorly from the superior surface 216 of the plate 212 adjacent to the outside edge 226 approximately midway between the anterior 228 and posterior 230 aspects of the plate 212. The outer stop 258 includes an inwardly projecting tab 260 spaced above and parallel to the superior surface 216 of the plate 212. The tab 260 includes a face 262 directed toward the articular surface component 214. At the extreme limits of motion of the articular surface component 214 toward the outside edge 226 of the plate 212, the articular surface component 214 will abut the face 262 of the outer stop 258 and stop its outward movement. The tab 260 is received in the circumferential groove 252 of the articular surface component 214 to prevent the outside edge 238 of the articular surface component 214 from moving vertically away from the base plate 212 such as by tipping. The face 262 of the tab 260 extends over a relatively short distance anterior-to-posterior such that it prevents outward movement of the articular surface component 214 primarily near the center portion of the plate 212 midway between the anterior 228 and posterior 230 aspects. The face 262 of the tab 260 is convex such that the constraint provided by the outer stop 258 and the rail 244 constrains the articular surface component 214 generally to motion in an arc from a posterior position near the outside edge 226 of the plate 212, to a midway position further from the outside edge 226 of the plate 212, to an anterior position again near the outside edge 226 of the plate 212. The circumferential groove 252, rail 244, and outer stop 258 may be sized with some gaps between them to permit some side-to-side motion of the articular surface component 214 within this general arc of motion.

FIGS. 10-12 depict a mobile bearing unicondylar tibial knee prosthesis 300 similar to that of FIGS. 7-9 including a tibial base plate component 312 and a tibial articular surface component 314. The base plate 312 is generally in the form of a generally flat, "D"-shaped plate having a smooth superior surface 316 for sliding engagement with the articular surface component 314 and an inferior surface 318 for engaging the bone. The inferior surface 318 includes pegs 320 and a fin 322 for insertion into the bone for enhanced fixation. The base plate 312 further includes an inside edge 324 that is positioned near the midline of the proximal tibia adjacent to the intercondylar eminence, an outside edge 326 that is positioned adjacent to the outer side (corresponding to the medial side of the knee for the illustrative prosthesis configured for the medial compartment of the knee) of the proximal tibia, an anterior aspect 328 that is positioned adjacent to the anterior side of the proximal tibia, and a posterior aspect 330 that is positioned adjacent to the posterior side of the proximal tibia.

The articular surface component 314 includes a superior surface 332 for articulation with a femoral component, an inferior surface 334 for sliding engagement with the superior surface 316 of the base plate 312, an inside edge 336, an outside edge 338, an anterior aspect 340, and a posterior aspect 342. The articular surface component 314 rests on the superior surface 316 of the base plate 312 and is generally free to slide from the anterior aspect 328 to the posterior aspect 330 of the base plate 312, to slide from the inside edge 324 to the outside edge 326 of the base plate 312, and to rotate on the base plate 312.

The base plate 312 further includes an inside rail 344 projecting superiorly from the superior surface 316 of the plate 312 to prevent the articular surface component 314 from impinging against the intercondylar eminence of the proximal tibia. The rail 344 includes an outwardly projecting tab 346 spaced above and parallel to the superior surface 316 of the plate 312. In the illustrative embodiment of FIGS. 10-12, the tab 346 is positioned vertically approximately midway up the rail 344. The tab 346 includes a face 350 extending from near the anterior aspect 328 of the plate 312 to near the posterior aspect 330 of the plate 312 and directed toward the articular surface component 314. At the extreme limits of motion of the articular surface component 314 toward the inside edge 324 of the plate 312, the articular surface component 314 will abut some portion of the rail 344 and stop its inward movement. The articular surface component 314 includes groove 352 along the inside edge 336 that receives the tab 346 to prevent the inside edge 336 of the articular surface component 314 from moving vertically away from the base plate 312 such as by tipping.

The base plate 312 further includes an optional outer stop 358 projecting superiorly from the superior surface 316 of the plate 312 adjacent to the outside edge 326 approximately midway between the anterior 328 and posterior 330 aspects of the plate 312. The outer stop 358 extends along a portion of the outside edge 326 and includes a concave, inwardly directed face 360 that is parallel to the curve of the outside edge 326. At the extreme limits of motion of the articular surface component 314 toward the outside edge 326 of the plate 312, the articular surface component 314 will abut the outer stop 358 and stop its outward movement. The face 360 of the outer stop 358 extends over a relatively long anterior-to-posterior distance such that it prevents outward movement of the articular surface component 314 over most of the anterior-to-posterior length of the plate 312. The concave face 360 of the outer stop 358 and the generally vertical face 350 of the rail 344 constrain the articular surface component 314 generally to motion within a "D"-shaped area. The side-to-side motion of the articular surface component 314 is more constrained near the anterior and posterior aspects 328, 330 of the plate 312 and is less constrained near the anterior-to-posterior center of the plate 312 where the outer 358 stop extends further from the inside rail 344.

The base plate 312 further includes an optional posterior stop 362 projecting superiorly from the superior surface 316 of the base plate 312 adjacent to the posterior aspect 330 of the plate 312 to prevent the articular surface component 314 from overhanging the posterior aspect 330 of the base plate 312. The posterior stop 362 presents a vertical face 364 facing anteriorly toward the articular surface component 314 against which the articular surface component 314 may abut. Other stops may optionally be provided. For example, an anterior stop (not shown) similar to the posterior stop 362 may be provided adjacent to the anterior aspect 328 of the plate 312.

FIGS. 13-15 depict a mobile bearing unicondylar tibial knee prosthesis 400 similar to that of FIGS. 10-12 including a tibial base plate component 412 and a tibial articular surface component 414. The base plate 412 is generally in the form of a generally flat, "D"-shaped plate having a smooth superior surface 416 for sliding engagement with the articular surface component 414 and an inferior surface 418 for engaging the bone. The inferior surface 418 includes pegs 420 and a fin 422 for insertion into the bone for enhanced fixation. The base plate 412 further includes an inside edge 424 that is positioned near the midline of the proximal tibia adjacent to the intercondylar eminence, an outside edge 426 that is positioned adjacent to the outer side of the proximal tibia, an anterior aspect 428 that is positioned adjacent to the anterior side of the proximal tibia, and a posterior aspect 430 that is positioned adjacent to the posterior side of the proximal tibia.

The articular surface component 414 includes a superior surface 432 for articulation with a femoral component, an inferior surface 434 for sliding engagement with the superior surface 416 of the base plate 412, an inside edge 436, an outside edge 438, an anterior aspect 440, and a posterior aspect 442. The articular surface component 414 rests on the superior surface 416 of the base plate 412 and is generally free to slide from the anterior aspect 428 to the posterior aspect 430 of the base plate 412, to slide from the inside edge 424 to the outside edge 426 of the base plate 412, and to rotate on the base plate 412.

The base plate 412 further includes an inside rail 444 projecting superiorly from the superior surface 416 of the plate 412 to prevent the articular surface component 414 from impinging against the intercondylar eminence of the proximal tibia. The rail 444 includes an opening 446 extending from the inside edge to the outside edge of the rail 444. The rail 444 includes a face 450 extending from near the anterior aspect 428 of the plate 412 to near the posterior aspect 430 of the plate 412 and directed toward the articular surface component 414. At the extreme limits of motion of the articular surface component 414 toward the inside edge 424 of the plate 412, the articular surface component 414 will abut some portion of the rail 444, such as the face 450, and stop its inward movement. The articular surface component 414 includes an inside tab 452 extending toward the inside edge 424 of the plate 412 and being received by the opening 446 in the rail 444 to prevent the inside edge 436 of the articular surface component 414 from moving vertically away from the base plate 412 such as by tipping.

The base plate 412 further includes an outer stop 458 projecting superiorly from the superior surface 416 of the plate 412 adjacent to the outside edge 426 approximately midway between the anterior 428 and posterior 430 aspects of the plate 412. The outer stop 458 includes an inwardly directed face 460 parallel to the outwardly directed face 450 of the inside rail 444. At the extreme limits of motion of the articular surface component 414 toward the outside edge 426 of the plate 412, the articular surface component 414 will abut some portion of the outer stop 458, such as the face 460, and stop its outward movement. The outer stop 458 includes an opening 462 extending from the outside edge to the inside edge of the stop 458. The articular surface component 414 includes an outside tab 466 extending toward the outside edge 426 of the plate 412 and being received by the opening 462 in the stop 458 to prevent the outside edge 438 of the articular surface component 414 from moving vertically away from the base plate 412 such as by tipping.

The outer stop 458 and the inside rail 444 constrain the articular surface component 414 generally to linear anterior-to-posterior motion. The width of the articular surface component 414 may be made less than the distance between the faces 450, 460 of the rail 44 and outer stop 458 to permit some side-to-side motion of the articular surface component 414 within this generally linear range of motion. The rail 444 and outer stop 458 may include anterior portions 468, 470 and posterior portions 472 that abut the tabs 452, 466 of the articular surface component 414 to limit anterior and posterior motion of the articular surface component and prevent it from overhanging the anterior and posterior aspects 428, 430 of the plate 412.

FIGS. 16-18 depict a mobile bearing unicondylar tibial knee prosthesis 500 similar to that of FIGS. 13-15 including a tibial base plate component 512 and a tibial articular surface component 514. The base plate 512 is generally in the form of a generally flat, "D"-shaped plate having a smooth superior surface 516 for sliding engagement with the articular surface component 514 and an inferior surface 518 for engaging the bone. The inferior surface 518 includes pegs 520 and a fin 522 for insertion into the bone for enhanced fixation. The base plate 512 further includes an inside edge 524 that is positioned near the midline of the proximal tibia adjacent to the intercondylar eminence, an outside edge 526 that is positioned adjacent to the outer side of the proximal tibia, an anterior aspect 528 that is positioned adjacent to the anterior side of the proximal tibia, and a posterior aspect 530 that is positioned adjacent to the posterior side of the proximal tibia.

The articular surface component 514 includes a superior surface 532 for articulation with a femoral component, an inferior surface 534 for sliding engagement with the superior surface 516 of the base plate 512, an inside edge 536, an outside edge 538, an anterior aspect 540, and a posterior aspect 542. The articular surface component 514 rests on the superior surface 516 of the base plate 512 and is generally free to slide from the anterior aspect 528 to the posterior aspect 530 of the base plate 512.

The base plate 512 further includes an inside rail 544 projecting superiorly from the superior surface 516 of the plate 512 to prevent the articular surface component 514 from impinging against the intercondylar eminence of the proximal tibia. The rail 544 includes an outwardly projecting tab 546 spaced above and parallel to the superior surface 516 of the plate 512. The tab is positioned vertically approximately midway up the rail 544. The tab 546 includes a face 550 extending from near the anterior aspect 528 of the plate 512 to near the posterior aspect 530 of the plate and directed toward the articular surface component 514. At the extreme limits of motion of the articular surface component 514 toward the inside edge 524 of the plate 512, the articular surface component 514 will abut some portion of the rail 544, such as the face 550, and stop its inward movement. The articular surface component 514 includes an inwardly facing groove 552 that receives the tab 546 to prevent the inside edge 536 of the articular surface component 514 from moving vertically away from the base plate 512 such as by tipping.

The base plate 512 further includes an outer stop 558 projecting superiorly from the superior surface 516 of the plate 512 adjacent to the outside edge 526 approximately midway between the anterior 528 and posterior 530 aspects of the plate 512. The outer stop 558 includes an inwardly projecting tab 560 spaced above and parallel to the superior surface 516 of the plate 512. The tab 560 includes a face 562 extending from near the anterior aspect 528 of the plate 512 to near the posterior aspect 530 of the plate parallel to the face 550 on the rail 544 and directed toward the articular surface component 514. At the extreme limits of motion of the articular surface component 514 toward the outside edge 526 of the plate 512, the articular surface component 514 will abut some portion of the outer stop 558, such as the face 562, and stop its outward movement. The articular surface component 514 includes an outwardly facing groove 564 that receives the tab 560 to prevent the outside edge 538 of the articular surface component 514 from moving vertically away from the base plate 512 such as by tipping.

The base plate 512 further includes a central rib 570 projecting superiorly from the superior surface 516 of the plate 512 and extending parallel to the faces 550, 562 down the center of the plate 512 from near the anterior aspect 528 to near the posterior aspect 530 of the plate 512. The rib 570 has a semi-circular cross section and is received in a matching groove 572 formed in the articular surface component 514. The outer stop 558, inside rail 544, and central rib 570 constrain the articular surface component 514 to generally linear anterior-to-posterior motion. The close fitting engagement of the tabs 546, 560 and grooves 552, 564 makes the articular surface component highly resistant to tipping. The illustrative embodiment depicts a male and female engagements between the plate 512 and articular surface component 514; however, the male and female components may be reversed and still fall within the scope of the invention.

It will be understood by those skilled in the art that the foregoing has described illustrative embodiments of the present invention and that variations may be made to these embodiments without departing from the spirit and scope of the invention defined by the appended claims.

What is claimed is:

1. A mobile bearing unicondylar tibial knee prosthesis configured to be positioned in a knee joint, the knee joint having a central plane that divides the knee joint into medial and lateral compartments, said prosthesis comprising:

a tibial base plate having a superior surface, an inferior surface, an inside edge configured to be positioned adjacent the central plane of the knee joint, an outside edge, an anterior aspect, a posterior aspect, and a stop projecting superiorly from the superior surface adjacent at least one of the inside edge and the outside edge, the stop having a curved surface having a first terminal end, a second terminal end, and a midpoint, the curved surface curving away from the inside edge of the tibial base plate from the midpoint to each of the terminal ends; and a tibial articular surface component comprising a superior surface, an inferior surface, an inside edge, an outside edge, an anterior aspect, and a posterior aspect, the inferior surface of the articular surface component engaging the superior surface of the base plate in sliding relationship, the curved surface of the stop of the tibial base plate and the tibial articular surface component defining a tab and groove engagement between them, the tab and groove engagement permitting the tibial articular surface component to slide anteriorly-posteriorly on the tibial base plate in a generally arc-shaped motion toward the outside edge of the base plate near the anterior and posterior aspects of the base plate, the articular surface component rotating about an axis offset from the central plane when the prosthesis is positioned in the knee joint, while restricting movement of the tibial articular surface component superiorly away from the base plate.

2. The prosthesis of claim 1 wherein the stop comprises an inside rail extending superiorly from the superior surface of the base plate adjacent to the inside edge, the rail including an outwardly projecting tab and the articular surface component including a groove engageable with the tab.

3. The prosthesis of claim 2 wherein the base plate further comprises an outer stop projecting superiorly from the superior surface of the base plate adjacent to the outside edge approximately midway between the anterior and posterior aspects of the plate to limit motion of the articular surface component toward the outside edge of the plate.

4. The prosthesis of claim 3 wherein the outer stop further comprises an inwardly projecting tab and the articular surface component includes a groove engageable with the tab of the outer stop.

5. The prosthesis of claim 4 wherein the outer stop extends over a relatively short distance anterior-to-posterior such that it limits outward movement of the articular surface component primarily near the center portion of the base plate approximately midway between the anterior and posterior aspects of the base plate.

6. The prosthesis of claim 5 wherein the rail curves toward the outside edge at an anterior portion and at a posterior portion, the curved anterior and posterior portions causing the articular surface component to slide outwardly away from the inside edge of the base plate at anterior and posterior positions of the articular surface component on the base plate such that the outer stop and rail constrain the articular surface component generally to arc-shaped motion from a posterior position near the outside edge of the plate, to a midway position further from the outside edge of the plate, to an anterior position again near the outside edge of the plate.

7. The prosthesis of claim 6 wherein the articular surface component, inside rail, and outer stop are sized to permit a predetermined amount of side-to-side motion of the articular surface component within the generally arc-shaped motion.

8. The prosthesis of claim 2 wherein the rail curves toward the outside edge at an anterior portion and at a posterior portion, the curved anterior and posterior portions causing the articular surface component to slide outwardly away from the inside edge of the base plate at anterior and posterior positions of the articular surface component on the base plate.

9. The prosthesis of claim 1 wherein the stop comprises an outer stop projecting superiorly from the superior surface of the base plate adjacent to the outside edge, the outer stop limiting motion of the articular surface component toward the outside edge of the base plate, the stop including an inwardly projecting tab and the articular surface component including a groove engageable with the tab.

\* \* \* \* \*